United States Patent
Paul et al.

[11] Patent Number: 6,166,393
[45] Date of Patent: Dec. 26, 2000

[54] METHOD AND APPARATUS FOR AUTOMATIC INSPECTION OF MOVING SURFACES

[75] Inventors: Detlef Paul, Stutensee, Germany; Ari Härkönen, Oulu, Finland; Pertti Kontio, Oulu, Finland; Timo Piironen, Oulu, Finland; Martti Karppinen, Oulu, Finland

[73] Assignees: Fraunhofer-Gesellschaft zur Förderung der angewandten, Germany; Spectra-Physics VisionTech Oy, Finland

[21] Appl. No.: 09/136,376

[22] Filed: Aug. 19, 1998

[30] Foreign Application Priority Data

Aug. 22, 1997 [EP] European Pat. Off. ............ 97114590

[51] Int. Cl.⁷ .................................................. G01N 21/89
[52] U.S. Cl. ................................ 250/559.08; 250/559.46; 356/237.5
[58] Field of Search ................................ 250/208.1, 226, 250/559.07, 559.08, 559.4, 559.41, 559.44, 559.45, 559.46, 559.22, 559.23, 559.24, 559.29, 559.31, 559.321; 356/372, 375, 376, 384, 385, 390, 392, 446, 237.1, 237.2, 237.3, 237.4, 237.5; 348/87, 88, 92, 93, 128, 131

[56] References Cited

U.S. PATENT DOCUMENTS

| | | |
|---|---|---|
| 4,595,289 | 6/1986 | Feldman et al. ................. 356/237.5 |
| 4,806,776 | 2/1989 | Kley ................................. 250/559.24 |
| 5,039,868 | 8/1991 | Kobayashi et al. . | 
| 5,248,876 | 9/1993 | Kerstens et al. . |
| 5,982,493 | 11/1999 | Lehnen et al. .................... 356/375 |

FOREIGN PATENT DOCUMENTS

| | | | |
|---|---|---|---|
| 59052735 | 3/1984 | European Pat. Off. | ....... G01N 21/88 |
| 61176825 | 8/1986 | European Pat. Off. | ........... G01J 3/50 |
| 06058731 | 3/1994 | European Pat. Off. | ........ G01B 11/24 |
| 32 42 447 A1 | 5/1984 | Germany | ........ G01N 21/89 |
| 195 11 534 A1 | 10/1996 | Germany | ........ G01N 21/88 |
| WO 92/00517 | 1/1992 | WIPO | .............. G01N 21/89 |
| WO 94/18643 | 8/1994 | WIPO | .............. G06K 9/00 |

OTHER PUBLICATIONS

Robert J. Woodham; "Determining Surface Curvature with Photometric Stereo"; 1989 IEEE International Conference on Robotics and Automation, Proceedings vol. 1; May 15–19, 1989; pp. 36–42, inclusive.

*Primary Examiner*—John R. Lee
*Attorney, Agent, or Firm*—Duft, Graziano & Forest, P.C.

[57] ABSTRACT

In a method an an apparatus for automatic inspection of moving surfaces using at least three different illumination/observation channels, the surface to be inspected under a bright field condition is illuminated by a first beam of light from a first light source. The light of the first beam of light reemitted from the surface is received by a light sensitive sensor device to obtain a first signal. Then, the surface is illuminated under a dark field condition by a second beam of light and by a third beam of light from a second and a third light source, respectively, the first, second and third beams of light having different characteristics. The light of the second beam of light and the light of the third beam of light, respectively, reemitted from the surface are received by the light sensitive sensor device to obtain a second signal and a third signal. Finally, a physical property of the surface is derived from the first, second and third signals.

22 Claims, 15 Drawing Sheets

METHOD AND APPARATUS FOR AUTOMATIC INSPECTION OF MOVING SURFACES

BACKGROUND OF THE INVENTION

1. Field of the Invention

The present invention relates to a method and to an apparatus for automatic inspection of moving surfaces, in particular to a method and an apparatus for automatic inspection of moving surfaces for applications such as the inspection of steel strips, wood, leather or tiles. Even more particular the present invention relates to a method and an apparatus for automatic inspection of moving surfaces using at least three different illumination/observation channels.

2. Description of Prior Art

Products like the above-mentioned steel strips, wood, leather or tiles are typically produced at high speed in a continuous process and they have to be inspected during motion. The defects which have to be detected and classified automatically are anomalies in the surfaces with respect to e.g. reflectivity, color, glossiness, texture and the 3D-profile of the surface under inspection.

In the prior art, systems for automatic surface inspection are well established and used for industrial applications such as the inspection of steel, tiles or wood. The applied cameras are monochrome or color line scan cameras. For illumination fluorescent lamps, halogen lamps or fiber optic illuminators are commonly used. The defects to be detected and classified are e.g. scratches, dents, knots and the like as defined by the application. Typically these defects manifest themselves in different ways, e.g. in deviations of reflectivity, glossiness, color, texture or the 3D-profile of the surface under inspection.

A critical part in the system design is to define the apparatus for image acquisition, including the selection of a camera and the illumination system, and to determine the geometrical relations of the components. The aim is to achieve images from the surface which contain the necessary information to detect and to distinguish all of the defects automatically, including 3D-defects. In many cases the result is disappointing. The reason is simply that monocular images do not contain reliable and unambiguous information on the 3D-profile and glossiness of the surface. To overcome this problem a multi-camera setup is used in some applications by means of which the surface is inspected under different viewing conditions simultaneously. In such setups, typically two monochromatic cameras and one illuminator are used to obtain bright and dark field images of the same object.

These setups suffer from a number of shortcomings: the alignment of two line scan cameras is difficult, and the mechanical constructions for these systems become heavy.

In the article by R. J. Woodham, "Photometric Method for Determining Surface Orientation from multiple Images", in Optical Engineering Vol. 19, 191, pp. 139 to 144, 1980, a photometric stereo technique is described. The principle of this technique is to take multiple images from the same object and with the same camera, and to vary the direction of the incident illumination between successive images, while holding the viewing geometry constant. This provides sufficient information to determine the surface orientation, i.e. to gather 3D-information, of each surface element of the inspected object at each image point.

The technique is named photometric stereo because it uses the radiance values recorded at a single pixel location in successive views, rather than the relative positions of displaced features in binocular stereo. Since the viewing geometry in this technique is not changed, the correspondence between pixels in the taken set of images is known a priori.

The photometric stereo method requires that the inspected object is resting, giving time to switch the lamps and to take the images, and that the reflectance distribution of the surface is known. Therefore, the method cannot be applied for inspection of moving materials and surfaces of unknown reflectivity.

DE 195 11 534 A1 relates to a method and an apparatus for detecting 3D-defects, such as dents and steps in a flat surface, in applications for automatic surface inspection, following the idea of photometric stereo. The surface under inspection is simultaneously illuminated with at least two lamps from different directions under dark field conditions, where the light from the lamps has different colors. A color line scan camera is used for image acquisition and 3D-defects are detected by analyzing the measured color values.

This method yields information on 3D-defects but not on glossiness and reflectivity of the surface because a symmetrical dark field illumination is used. Therefore, the capabilities for discriminating between different types of defects are limited. Furthermore, defect detection is done by a color classifier. Using this method it is not possible to adapt to a changing appearance of the inspected surface or to changes of the illumination. In practical applications, the sensitivity for defect detection is limited.

EP 0 764 845 A2 describes an apparatus for image acquisition which is similar to the one described in DE 195 11 534 A1, but the method for the detection of 3D-defects is only based on shadows, which can be observed at the edges of steps in the surface.

In the article by M. Magee et al., "Identification of Flaws in Metallic Surfaces Using Specular and Diffuse Bispectral Light Sources" in SPIE, Vol. 1825, Intelligent Robots and Computer Vision XI, pp. 455 to 468, 1992, a method for identification of flaws in metallic surfaces is described. The aim of this method is to enhance contrast and detection rate for scratches during automatic surface inspection of resting cast metal parts. The object under inspection is illuminated with light of different colors: there is one channel for a dark field using a very shallow angle of incidence and one channel for bright field. The used effect is that the light from the shallow dark field illumination will be scattered by sharp edges of the scratches and therefore scratches will look dark in the bright field and bright in the dark field. A second channel for dark field illumination is missing and it is therefore not possible to estimate the slope of surface elements on surfaces with varying glossiness and reflectivity.

SUMMARY OF THE INVENTION

Starting from this prior art it is the object of the present invention to provide an enhanced method and apparatus for automatic inspection of surfaces which enables the inspection of surfaces with enhanced reliability at less false alarm rates.

In accordance with a first aspect of the present invention, this object is achieved by a method for automatic inspection of moving surfaces using at least three different illumination/observation channels, said method comprising the steps of:

a) illuminating said surface to be inspected under a bright field condition by a first beam of light from a first light source, and receiving light of the first beam of light reemitted from said surface by a light sensitive sensor device to obtain a first signal;

b) illuminating said surface under a dark field condition by a second beam of light and by a third beam of light from a second and a third light source, respectively, said first, second and third beams of light having different characteristics, and receiving light of the second beam of light and light of the third beam of light, respectively, reemitted from said surface by said light sensitive sensor device to obtain a second signal and a third signal; and c) deriving from said first, second and third signals a physical property of said surface.

In accordance with a second aspect of the present invention, this object is achieved by a method for automatic inspection of moving surfaces using at least three different illumination/observation channels, said method comprising the steps of:

a) illuminating said surface by a beam of light from a light source;

b) receiving light of a first characteristic reemitted from said surface under a bright field condition by a first light sensitive sensor device to obtain a first signal;

c) receiving light of a second and a third characteristic, respectively, reemitted from said surface under a dark field condition by a second and a third light sensitive sensor device to obtain a second signal and a third signal, said first, second and third light sensitive sensor devices being spatially separated from each other; and d) deriving from said first, second and third signals a physical property of said surface.

In accordance with a third aspect of the present invention, this object is achieved by an apparatus for automatic inspection of moving surfaces, comprising:

a first light source illuminating said surface with light of a first spectral characteristic under a bright field condition;

a light sensitive sensor device receiving reemitted light of the first spectral characteristic to obtain a first signal;

a second light source illuminating said surface with light of a second spectral characteristic under a dark field condition, said second spectral characteristic being different from said first spectral characteristic, said light sensitive sensor device receiving reemitted light of the second spectral characteristic to obtain a second signal;

a third light source illuminating said surface with light of a third spectral characteristic under a dark field condition, said third spectral characteristic being different from said first and second spectral characteristics, said light sensitive sensor device receiving reemitted light of the third spectral characteristic to obtain a third signal; and means for deriving a physical property of said surface from said first, second, and third signals.

In accordance with a fourth aspect of the present invention, this object is achieved by an apparatus for automatic inspection of moving surfaces, comprising:

a light source for illuminating said surface;

a first light sensitive sensor device receiving light of a first spectral characteristic reemitted from said surface under a bright field condition to obtain a first signal;

a second light sensitive sensor device receiving light of a second spectral characteristic reemitted from said surface under a dark field condition to obtain a second signal, said second spectral characteristic being different from said first spectral characteristic;

a third light sensitive sensor device receiving light of a third spectral characteristic reemitted from said surface under a dark field condition to obtain a third signal, said third spectral characteristic being different from said first and second spectral characteristic, said first, second and third light sensitive sensor devices being spatially separated from each other; and means for deriving a physical property of said surface from said first, second, and third signals.

The present invention provides a method and an apparatus for automatic surface inspection which makes it possible to extract and to process information on the physical properties of the surface, like reflectivity, glossiness and slope of surface elements separately. The advantage is that especially 3D-defects can be detected and classified with high reliability even in textured surfaces. Applications are e.g. the inspection of steel, leather, wood, extruded profiles or other materials, which are produced in a continuous process with a high speed and have to be inspected during motion.

The present invention is based on the idea of photometric stereo. Information on reflectivity, color, glossiness and profile of the inspected surface is captured, e.g. by an apparatus comprising a color line scan camera and at least three spatially separated light sources with different spectral characteristics. The result of the image acquisition are registered images, e.g. R-, G-, B-images, basically corresponding to the channels of illumination. These images are processed in several steps comprising estimation of physical properties for each surface element, detection of surface anomalies, feature extraction and classification.

According to a preferred embodiment of the present invention the first illumination/observation channel is formed by a light sensitive sensor device and a first light source, the second illumination/observation channel is formed by the same light sensitive sensor device and by a second light source, and the third illumination/observation channel is formed by the same light sensitive sensor device and a third light source.

According to another embodiment of the present invention the first illumination/observation channel is formed by a first light sensitive sensor device and by a light source, the second illumination/observation channel is formed by a second light sensitive sensor device and the same light source, and the third illumination/observation channel is formed by a third light sensitive device and the same light source.

According to a further embodiment of the invention information on reflectivity, glossiness and slope from a moving surface are extracted separately from the surface element under inspection and based on this information the surfaces are inspected with enhanced reliability at less false alarm rate. In particular, it is possible to discriminate between 3D-defects and accepted variations within the appearance of the surface.

Further preferred embodiments are defined in the dependent claims.

BRIEF DESCRIPTION OF THE DRAWINGS

In the following, preferred embodiments of the inventive method and the inventive apparatus will be described with reference to the accompanying drawings, in which

FIG. 7b shows a side view of the apparatus of the FIG. 7a;

DESCRIPTION OF PREFERRED EMBODIMENTS OF THE INVENTION

Figure 1:
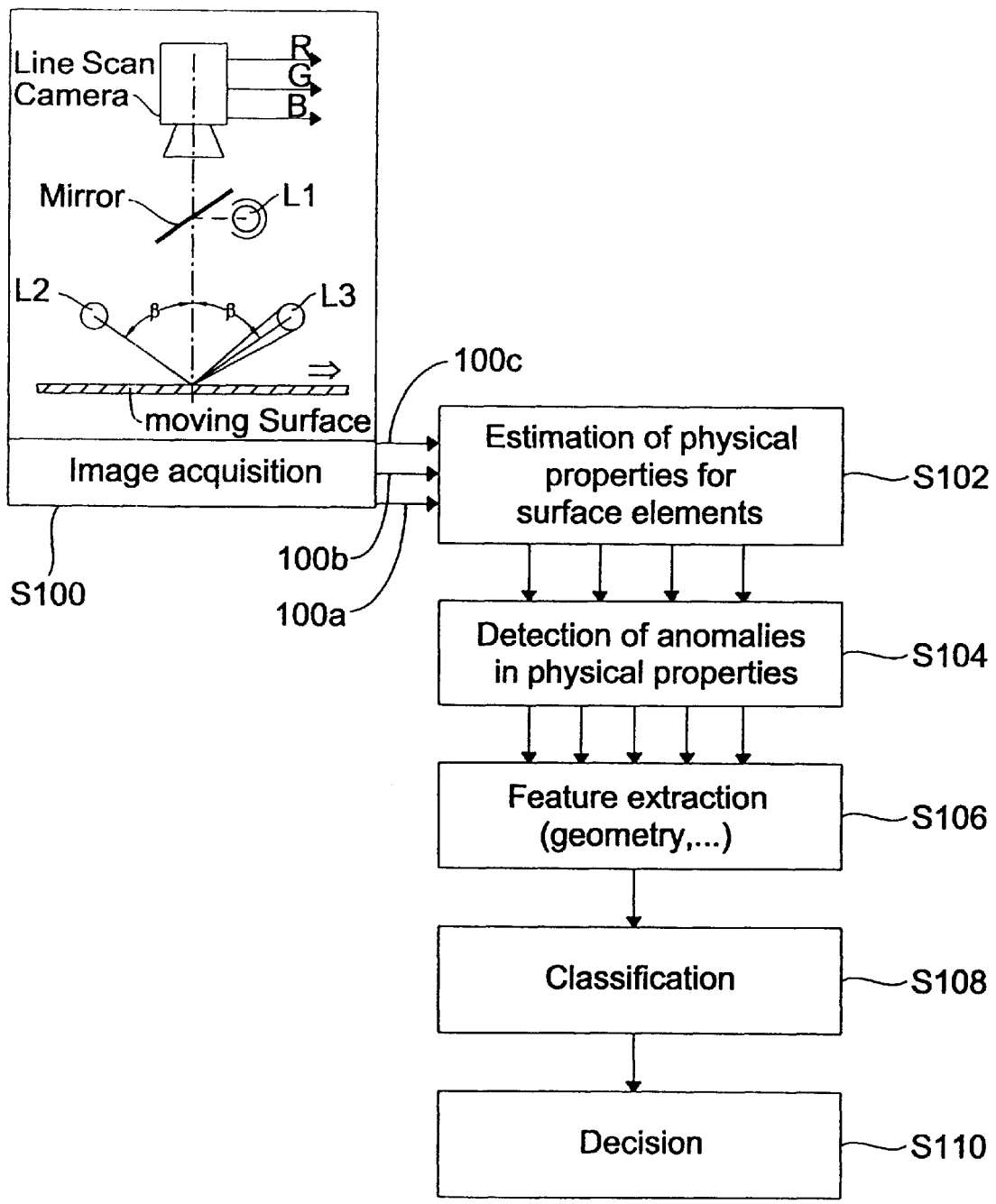
FIG. 1 shows the overall concept underlying the method and the apparatus of the present invention.

With respect to FIG. 1 the overall concept underlying the inventive method and the inventive apparatus for automatic inspection of surfaces will be described. With the measurement step S100 an image of the moving surface under inspection is acquired. The apparatus schematically shown at step S100 in FIG. 1 will be described with reference to FIG. 3 hereinafter. In step S102 physical properties of the inspected surface element are estimated on the basis of the acquired image. In step S104 anomalies in the physical properties of the surface are detected. In step S106 specific features are extracted and in step S108 the detected regions are classified. Finally in step S110 a decision is made whether the inspected surface is acceptable, i.e. fulfills predetermined requirements with respect to the physical properties, or whether the surface exhibits defects.

According to the present invention the image acquired in step S100 is formed from three different images which is illustrated by the arrows 100a, 100b and 100c between step S100 and step S102. The three images are represented by three video signals, wherein a first signal 100a representing a first image is obtained by observing the surface to be inspected under a first observation condition by means of a first of at least three different illumination/observation channels. The second and the third signals on line 100b and 100c, respectively, are obtained by observing the surface under a second observation condition by means of a second and a third of the at least three different illumination/observation channels. On the basis of the thus obtained first, second and third signals physical properties of the surface elements are derived in step S102.

According to a preferred embodiment of the present invention information on reflectivity, color, glossiness and profile of the inspected surface is captured by an apparatus with a color line scan camera and three spatially separated light sources with different spectral characteristics, following the above outlined idea of photometric stereo. The result of the image acquisition in step S100 are in this embodiment three registered images (R, G, B) basically corresponding to three channels of illumination. In the above described steps the images are processed as follows:

In step S102 the physical property or properties for each surface element are estimated and the result are physical property images representing reflectivity, color, glossiness and slope of the surface element, as it is illustrated by the four arrows between block S102 and block S104. These images have the same spatial resolution as the original image.

In step S104 the anomalies are detected. Local anomalies within the property images are detected at the same spatial resolution as the original image, and regional anomalies, e.g. due to a shallow wave in the surface or surface roughness, are detected by computing the moving average or the moving standard deviation of the slope of the surface elements followed by a comparison of the resulting statistical figures with thresholds. The output of step S 104 are multiple binary images, as indicated by the plurality of arrows connecting step S104 and step S106.

In step S106 features from the binary images generated in step S104 are extracted. Simple or complex geometrical features are calculated, such as the area and shape of blobs in the binary images. In addition, neighborhood relations can be taken into account, e.g. accumulation of blobs, or the overlap of blobs within different layers of the multiple binary images received from step S104.

In step S108 the classification is carried out and the segmented regions of the detection image are classified due to the extracted features.

Prior to describing preferred embodiments of the inventive apparatus and the inventive method, with respect to FIG. 2 it is illustrated how light is scattered dependent from the reflectivity, glossiness and slope, respectively, of a surface.

The apparatus according to the present invention which is used for image acquisition is, according to a preferred embodiment, intended to gather information on reflectivity, glossiness, color and slope of the surface elements under inspection. The apparatus and method described below are based on considerations as illustrated in FIG. 2 which shows the way how light will be scattered from a surface element if it is illuminated by a ray of light which is incident orthogonal to the inspected surface.

Figure 2A:
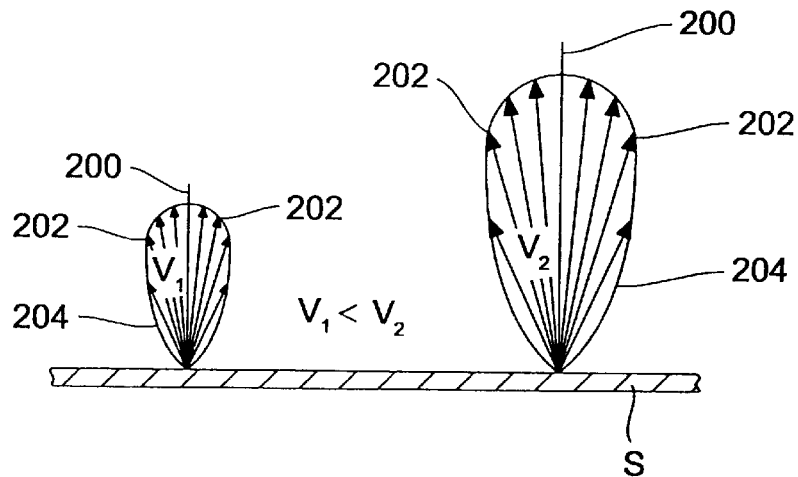
FIGS. 2a–c illustrate how light is scattered from a surface dependent from the reflectivity, glossiness and slope, respectively, of the surface.

In FIG. 2a the scattering characteristics with respect to the reflectivity of a surface S are shown. In FIG. 2a a beam of light 200 is incident orthogonal to the surface S and light beams 202 are reemitted from the surface S. As can be seen from FIG. 2a a line 204 is drawn around the reemitted beams 202 indicating the lobe of the reflected light. As can be seen from FIG. 2a for a low reflectivity of the surface S (left-hand side of FIG. 2a) the energy of the reemitted light will be low, as it is indicated by the small lobe 204 indicating a low volume $V_1$ of the reflected light distribution. In case of a high reflectivity of surface S the energy of reemitted light will be high, as it is illustrated by the large lobe 204, i.e. the volume $V_2$ of the reflected light distribution is high. As can be seen from FIG. 2a the shape of the light distribution, i.e. the lobes 204, will be the same.

Figure 2B:
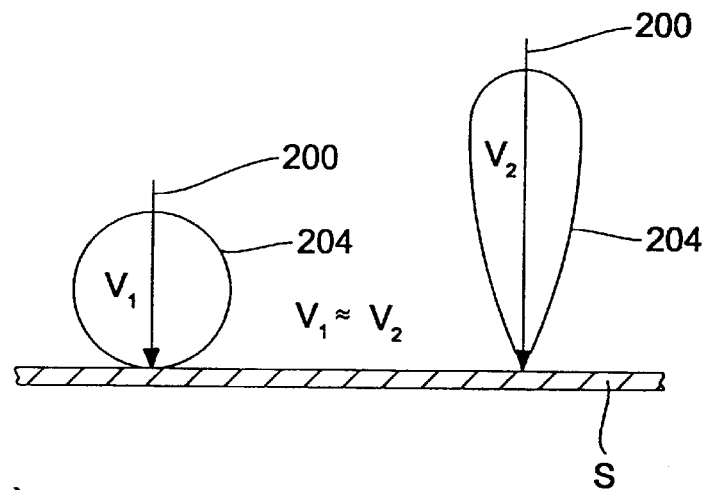

With respect to FIG. 2b the light distribution of the reemitted light for a different glossiness of the surface S is illustrated. Again a beam light of 200 is incident orthogonal to the surface S. In case of a low glossiness of the surface S (left-hand side of FIG. 2b) the light distribution as indicated by lobe 204 will be broad. For a high glossiness of surface S (right-hand side of FIG. 2b) the light distribution, again indicated by lobe 204, will be slim. The reflected light distribution indicated by the volumes $V_1$ and $V_2$ is supposed to be the same in case of a low glossiness of the surface S and for a surface S of high glossiness in this example.

Figure 2C:
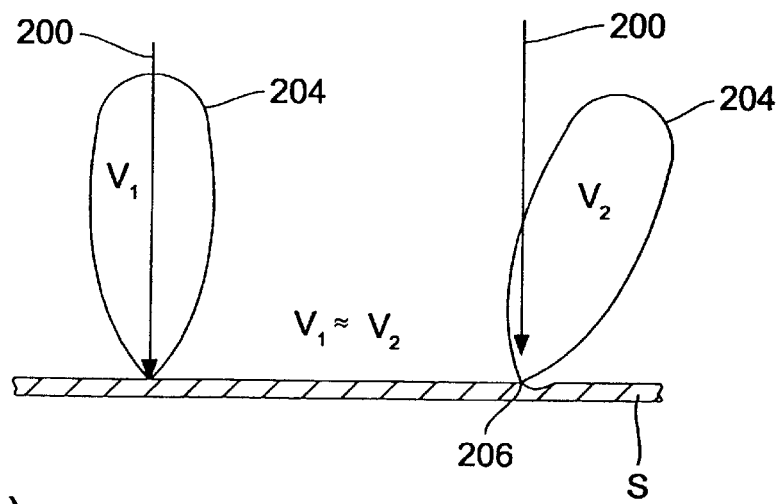

In FIG. 2c the reflected light distribution in case of a slope in surface S is shown. Again a beam of light 200 is incident orthogonal to surface S and the reflected light distribution is again indicated by lobe 204, whereas the amount of reflected light is again indicated by the volumes $V_1$ and $V_2$. For a horizontal surface element, the light distribution 204 will be symmetrical with respect to the surface normal, and it will be tilted if the surface element S has a slope 206. The volumes $V_1$ and $V_2$ are the same in both cases.

The different shapes of the lobes 204 and volumes $V_1$, $V_2$ of the reemitted light distribution can be discriminated by simultaneously observing the illuminated surface element with several light sensitive sensors from different directions. The same will be true, if the light source used in FIG. 2 for illuminating the surface S with the beam of light 200 is replaced by a single light sensitive sensor, like a camera, and if the sensors are replaced by light sources.

The apparatus for image acquisition achieved by the abovementioned replacement will be described in more detail in FIG. 3.

Figure 3:
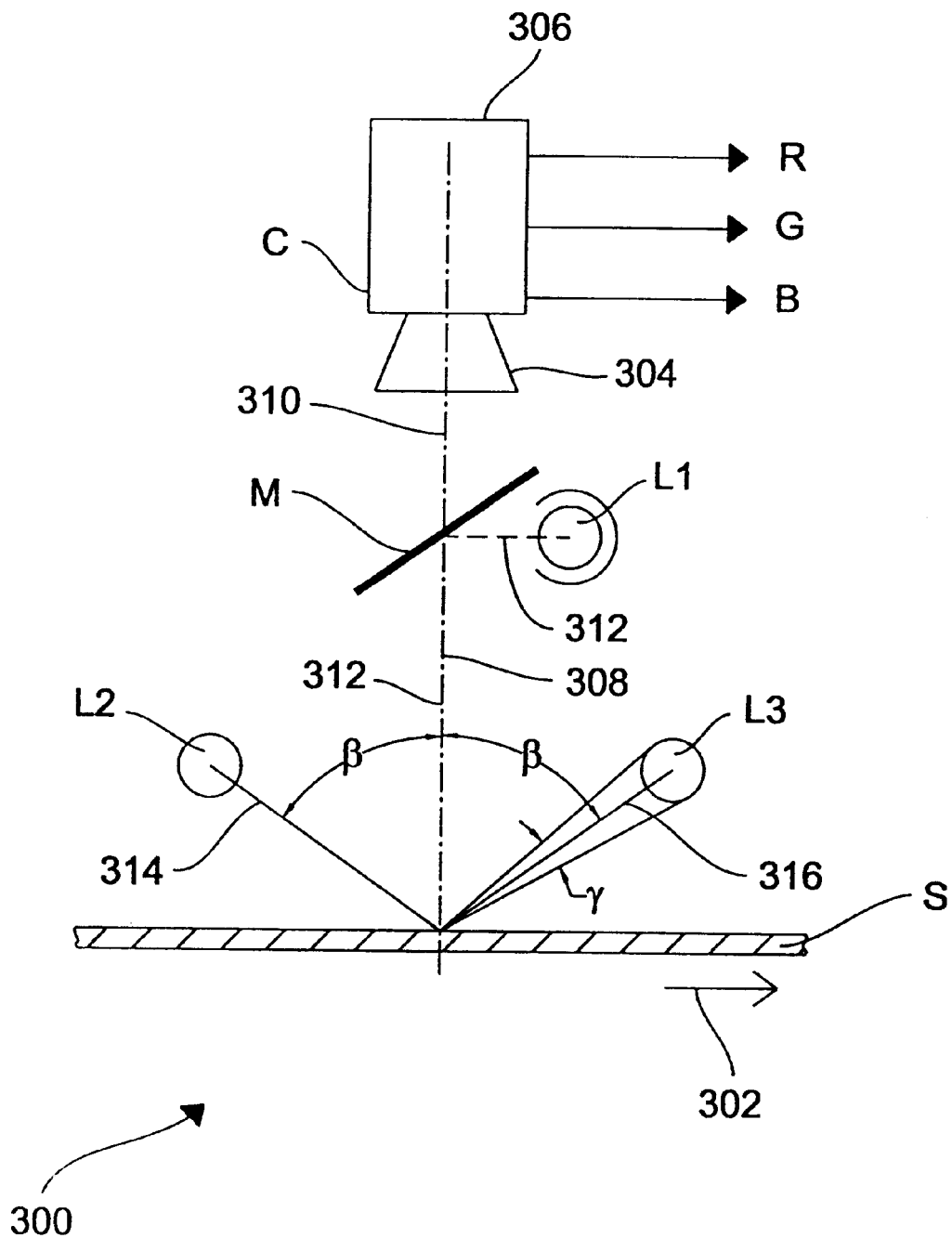
FIG. 3 shows a first embodiment of the inventive apparatus.

The apparatus in FIG. 3 is one preferred embodiment of the present invention and is indicated by reference sign 300. The apparatus 300 comprises a camera C which is a color line scan camera. The camera C comprises a lens 304 and a processing section 306 for generating signals representing the received images. Section 306 has three outputs R, G, B wherein the signals are representing a red image (R), a green image (G) and a blue image (B). The camera C is arranged above the surface S to be inspected in such manner that the normal 308 of surface S is coincident with the axis of observation 310 of the camera C.

Further three light sources L1, L2 and L3 emitting light beams 312, 314 and 316 of different spectral characteristics are provided. Light from the respective light sources is viewn under an angle v by the inspected line of the surface. The light beams 312 from the first light source L1 are directed via a mirror M towards the surface S in such a manner that they are incident orthogonal onto surface S. The light sources L2 and L3 are arranged such that the respective beams of light 314 and 316 emitted from the light sources enclose with the normal 308 of the surface S an angle β.

Light source L1 is illuminating surface S under bright field conditions by means of the mirror M, which can be a beam splitting mirror. Light sources L2 and L3 illuminate the surface S under symmetrical dark field conditions. A bright field condition is a condition under which light emitted, e.g. by light source L1, is reflected from a specular surface S back towards the lens 304 of camera C. A dark field condition is a condition under which, in case of a non-defective surface, light, e.g. emitted by light source L2 is not reflected towards the lens 304 of camera C from a specular surface. The angle β and v can be chosen in accordance with the demands of the application for optimized sensitivity and robustness of the measurements. E.g. for glossy surfaces β has to be small.

In most applications it will be possible to avoid the beam splitting mirror M and to use a non-symmetrical arrangement for image acquisition. Such an arrangement is shown as a further embodiment of the inventive apparatus in FIG. 4.

Figure 4:
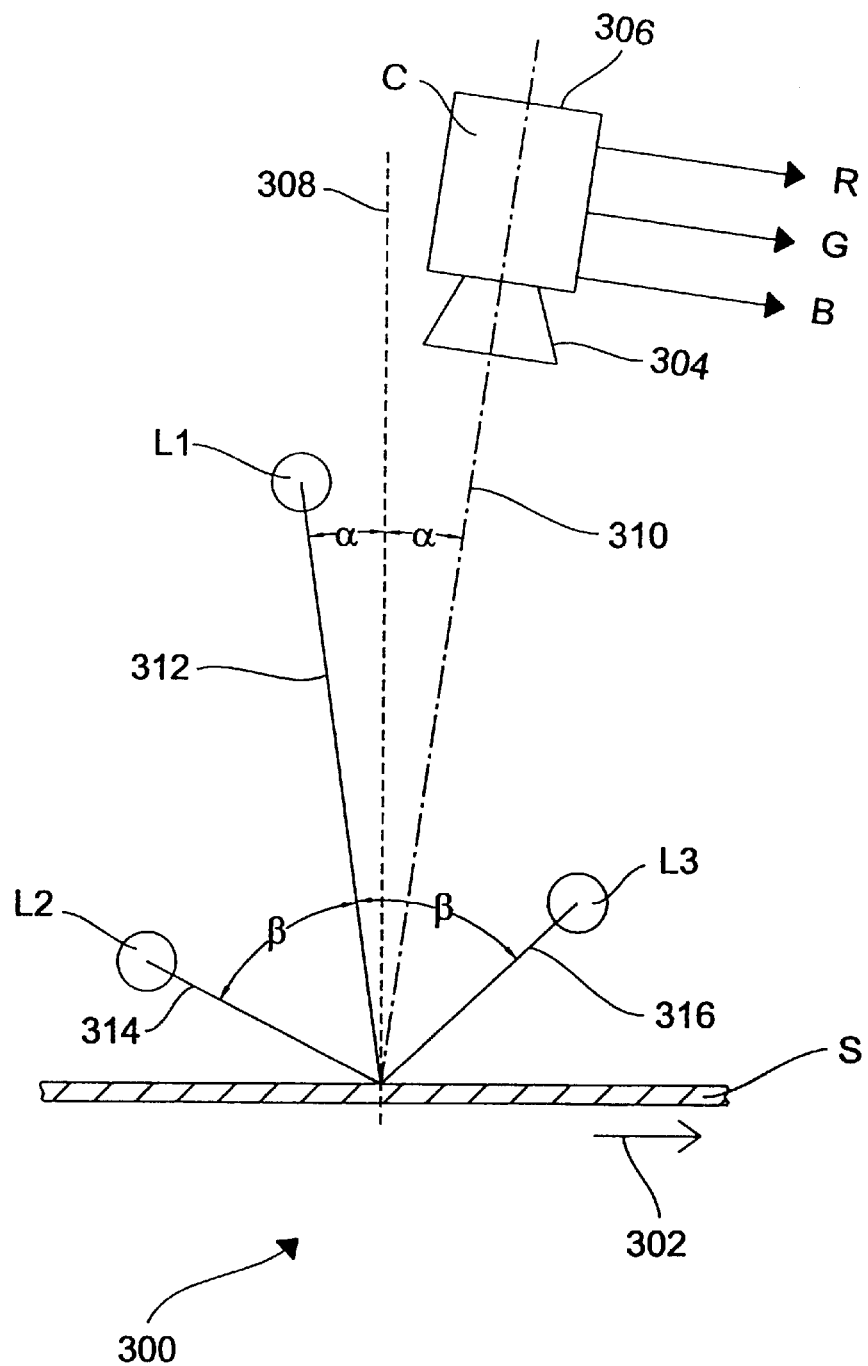
FIG. 4 shows a second embodiment of the inventive apparatus.

In FIG. 4 the same reference signs are used for identical elements, which have already been described with reference to FIG. 3. The difference between the apparatus shown in FIG. 4 and the apparatus shown in FIG. 3 is that the axis of observation 310 of camera C and the beams of light 312 emitted from light source L1 are not coincident with the normal 308 of surface S. The axis of observation 310 and normal 308 as well as the beams of light 312 of light source L1 and the normal 308 enclose an angle a.

With respect to the above description of the inventive method and the inventive apparatus it becomes clear from the description of the embodiments of FIG. 3 and 4 that in these embodiments three different illumination/observation channels are used wherein the first illumination/observation channel is formed by a light sensitive sensor device which is according to FIG. 3 and 4 the camera C and by the first light source L1, wherein the camera C receives light of the first beam 312 of light reemitted from the surface element S. The second illumination/observation channel is formed by the light sensitive sensor device C and the second light source L2 and the light sensitive sensor device or camera C receives light of the second beam 314 of light reemitted from the surface element S. The third illumination/observation channel is formed by the light sensitive sensor device or camera C and the third light source L3, and the camera C receives light of the third beam 316 of light reemitted from the surface element S. In the embodiments described with reference to FIG. 3 and 4 the three beams 312, 314 and 316 of light all have different characteristics, and according to a specific embodiment have different spectral characteristics, i.e. different colors. In the embodiment described with reference to FIG. 3 and 4 the second light source L2 and third light source L3 operating under a dark field condition are arranged symmetrically with respect to the normal 308 of surface S or with respect to the first beam of light 312 emitted from the first light source L1. It is, however, noted that the light sources L2 and L3 can be arranged in a non-symmetrically manner. As to the position of the first lamp L1 it is noted that same may deviate somewhat from the exact specular direction shown in FIG. 4 without disturbing the bright field condition. Further to the described embodiment, the second and the third light source can be symmetrically arranged with respect to the normal 308 of the surface S or with respect to the first beam of light 312 emitted from the first light source L1.

The above described principle underlying the present invention is, however, not restricted to three channels of illumination and three color channels of the camera, or more broadly speaking to only three illumination/observation channels, but can be extended to N channels of illumination and observation.

The light sources L1, L2 and L3 may be simply colored fluorescent lamps. They can also be rows of halogen lamps equipped with color filters, or they can be built by using collimated fibre optics. The latter realization has the advantage of a very bright and even illumination of the inspected line of surface S, which is necessary in high speed applications, especially because the dark field illumination used in photometric stereo requires a lot of light. Besides the above mentioned fluorescent lamps, any incandescant lamp, gas discharge lamps (colored or wide spectrum), LEDs, and Lasers can be used for illuminating the surface.

The three characteristic angles a, β and v in the apparatus for image acquisition as shown in FIG. 3 and FIG. 4 can be chosen independently in any of the mentioned relationships for illumination. The angle v has to be selected carefully in order to detect shiny defects. When using fluorescent tubes, this angle can be determined by changing the distance between the lamps and the inspected surface or by adding mirrors behind the lamps or by adding more fluorescent tubes.

The used light sources are not point light sources but are somewhat expanded. In FIG. 3 it is assumed that fluorescent tubes are used which extend perpendicular to the direction of motion of the surface. In the direction of motion of the surface the extension is defined by the diameter of the tubes. Based on the distance of the tubes from the observed line on the surface and the diameter of the tubes the angle v (gamma) is determined under which the surface is illuminated by light. It is preferred that the angle v can be varied as shown in FIG. 5. In case of fluorescent tubes this variation can be achieved by changing the distance between the tubes and the surface, by partially covering the tubes or, as shown in FIG. 5, by arranging a plurality of tubes in parallel.

Corresponding measures can be taken if collimated fibre line optics are applied.

With respect to FIG. 5 the illumination under dark field conditions is explained in more detail.

Figure 5A:
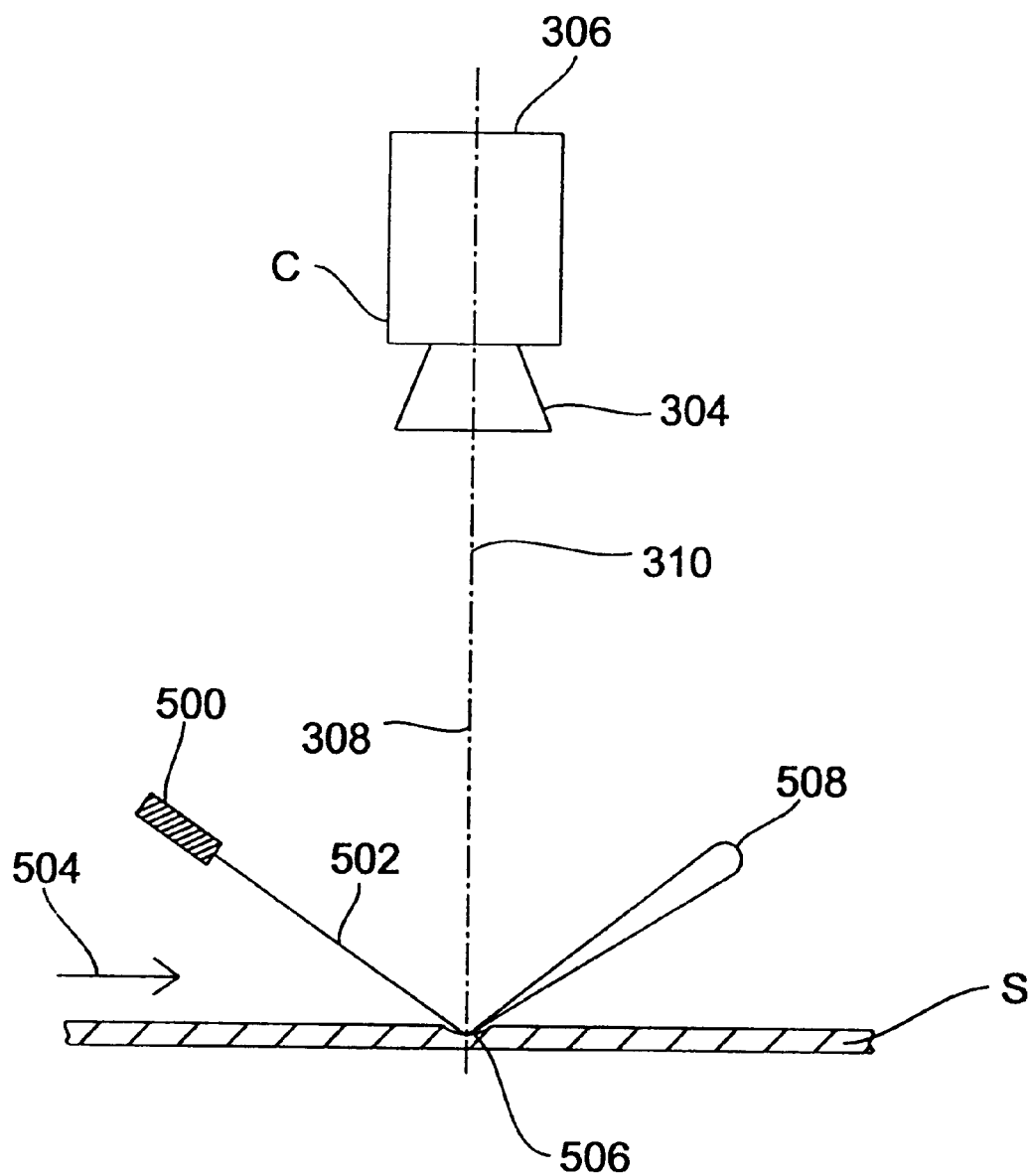
FIGS. 5a and b illustrate the influence of the angle of illumination for detection of 3D-defects in specular surfaces under dark field condition.

In FIG. 5a a light source 500 emitting a beam of light 502 is used for illuminating a surface S which is moved into a direction which is indicated by arrow 504. The incident beam of light 502 is reflected at a defect portion 506 of surface S and the distribution of the reflected light energy is indicated by means of lobe 508. The camera C is arranged above the surface S in such a manner that its axis of observation 310 is coincident with the normal 308 of surface S.

Figure 5B:
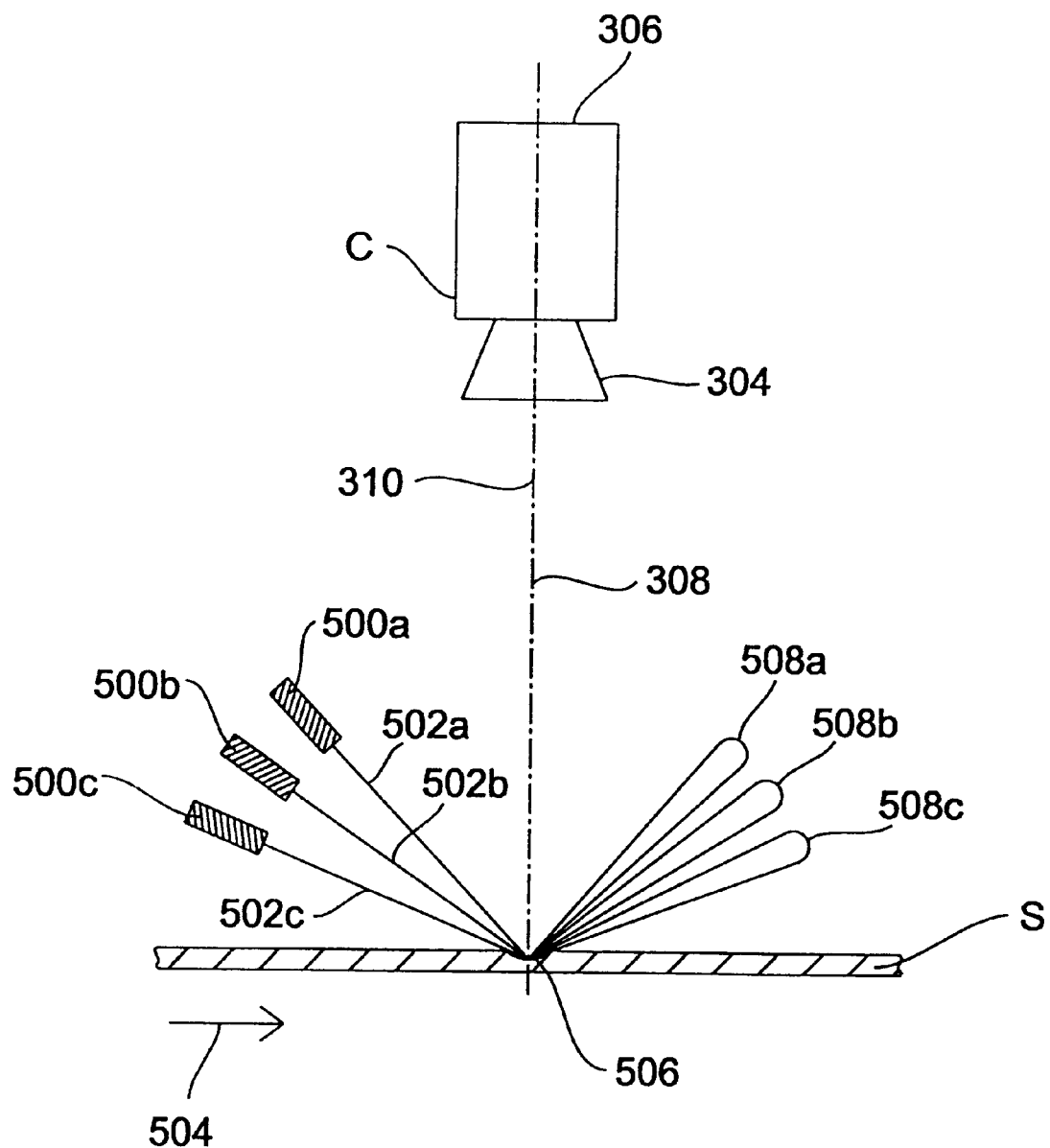

In FIG. 5b a similar arrangement is shown, in which the light source 500 is replaced by three light sources 500a, 500b and 500c emitting respective beams of light 502a, 502b and 502c which results in a distribution of the reflected energy as indicated by lobes 508a, 508b and 508c. The light sources 500a, 500b and 500c are formed by a multiple fibre optic. From a comparison of FIG. 5a and 5b it becomes clear that a wide angle dark field illumination with multiple fibre optics as shown in FIG. 5b is to be preferred, since the benefits of such an arrangement are an enhanced light level of the illumination and an enhanced probability for detection of reflections from shiny defects.

It is to be noted that instead of using one illuminator/color a number of illuminators of the same color can be used when their difference of space angle is kept relatively small. This can even result in better defect contrast on some materials.

With an apparatus for image acquisition as it is described with reference to FIGS. 3 and 4, sloping surface elements or steps in the surface under inspection will only be detected if the surface normal 308 has a component which is orientated in the direction 302 of surface motion. Steps, which are orientated parallel to the direction 302 of motion, cannot be detected. This makes such an apparatus well suited even for the inspection of profiled material, such as extruded profiles, but the apparatus is not suited for applications, where down web orientated 3D-defects might occur and have to be detected. For such applications, the incident light from the dark field illuminators should be orientated cross to the direction of motion, rather than parallel. Such a type of illumination can be realized by a side illumination, which will be described subsequently in more detail with reference to FIG. 6.

Figure 6:
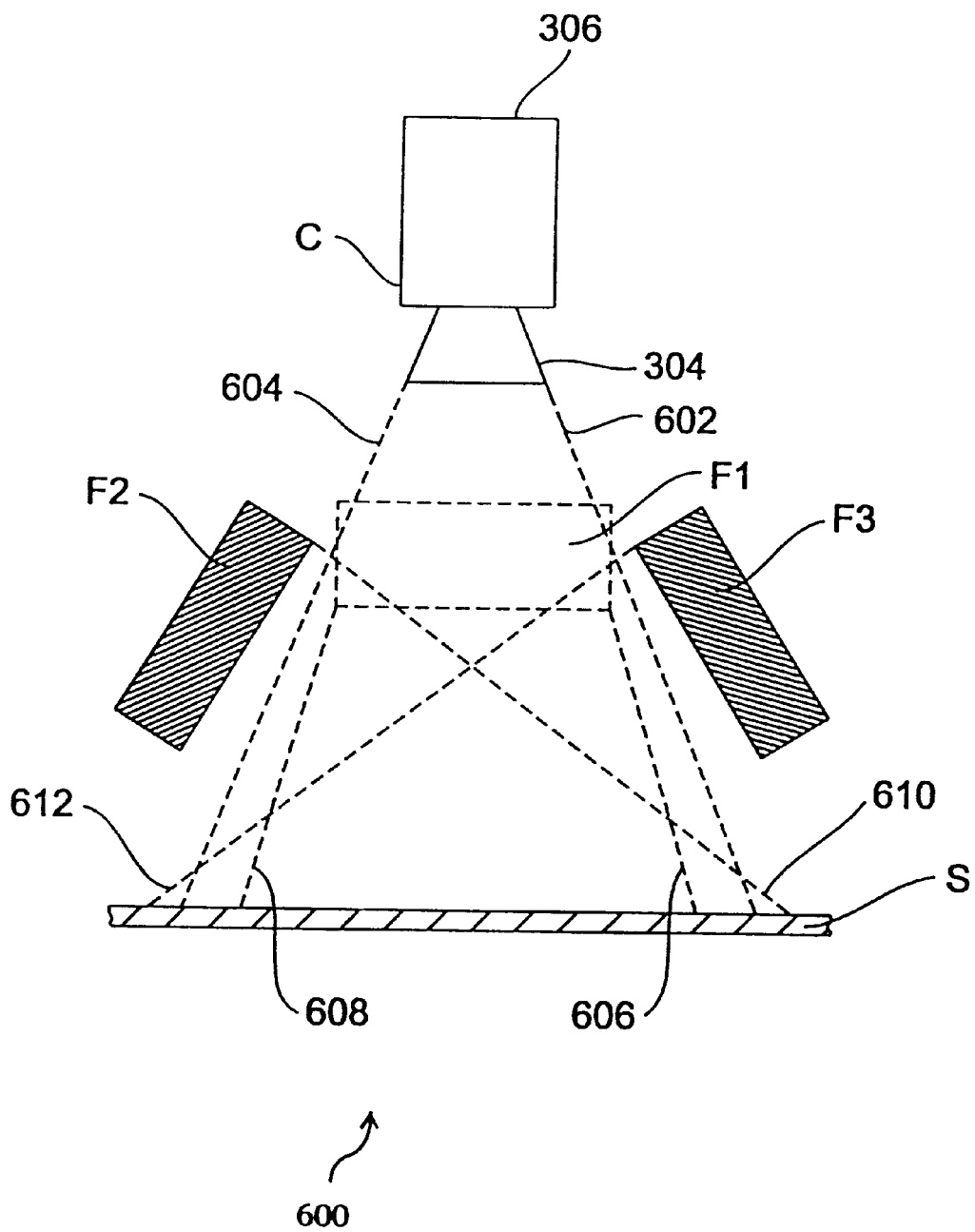
FIG. 6 shows an arrangement of the light sources for detecting 3D-defects in the surface which are orientated perpendicular to the direction of motion of the surface.

The apparatus 600 comprises the camera C which is arranged above the surface S, the direction of motion of surface S would be out of the plane of FIG. 6. Instead of the light sources L1 to L3 used in the embodiments described with reference to FIG. 3 and 4, the apparatus 600 comprises three standard fibre illuminators F1, F2 and F3. In FIG. 6 the field of observation of the camera C is limited as shown by the two dashed lines 602 and 604. As can be seen from FIG. 6 the illumination range of fibre illuminator F1 indicated by dashed lines 606 and 608 is such that light from the first illuminator F1 which is reflected b y the surface S is directed towards camera C such that illuminator F1 operates under a bright field condition. Fibre illuminator F2 has a range in which light is emitted, which is limited as indicated by dashed line 610, and illuminator F3 has a range of illuminating the surface S which is limited as indicated by dashed line 612. Illuminators F2 and F3 operate under a dark field condition, i.e. in case of a non-defective surface, the light from illuminators F2 and F3 reflected by a specular surface S is not directed towards the lens 304 of camera C. The indicated range of illumination of illuminators F2 and F3 is achieved by arranging same in a tilted position under a required illumination angle. Illuminator F1 may be aligned with camera C. Basically the bright field illuminator F1 is positioned in the same way as the light source or lamp L1 is in FIG. 4. Instead of fibre illuminators F1, F2 and F3, illuminators like halogen lamps with color filters can be used.

This construction is not sensitive to height variations and vibrations of the surface, but suffers from a sloping illumination profile. Depending on the reflectivity of the surface this may or may not be problematic. If the surface is not very specular, the uneven illumination can be compensated by a proper correction of the resulting video signal, without loosing a lot of dynamic range at the borders of the illuminated area.

With respect to FIG. 7 a preferred embodiment of a side illumination is described.

Figure 7A:
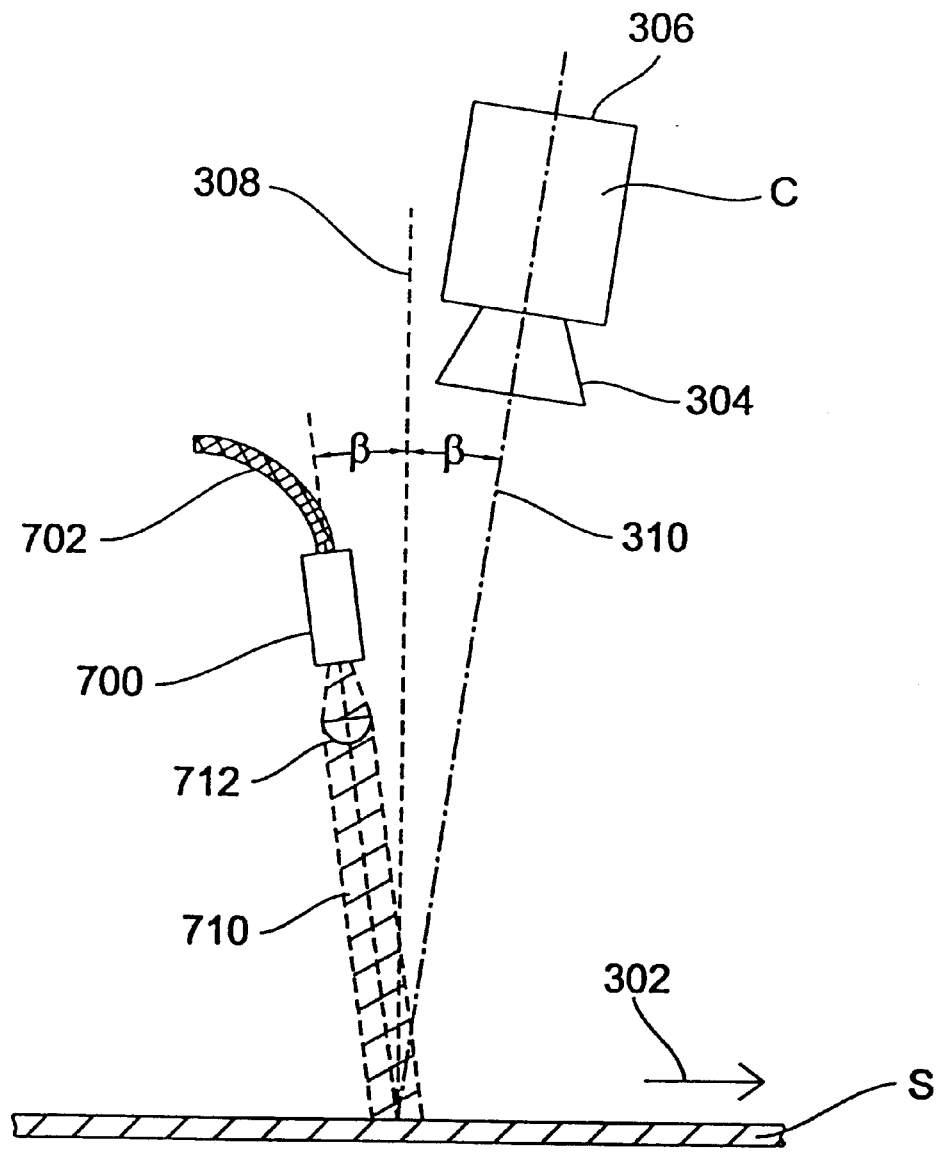
FIG. 7a shows a preferred embodiment of the inventive apparatus with integrated fibre optics.
Figure 7B:
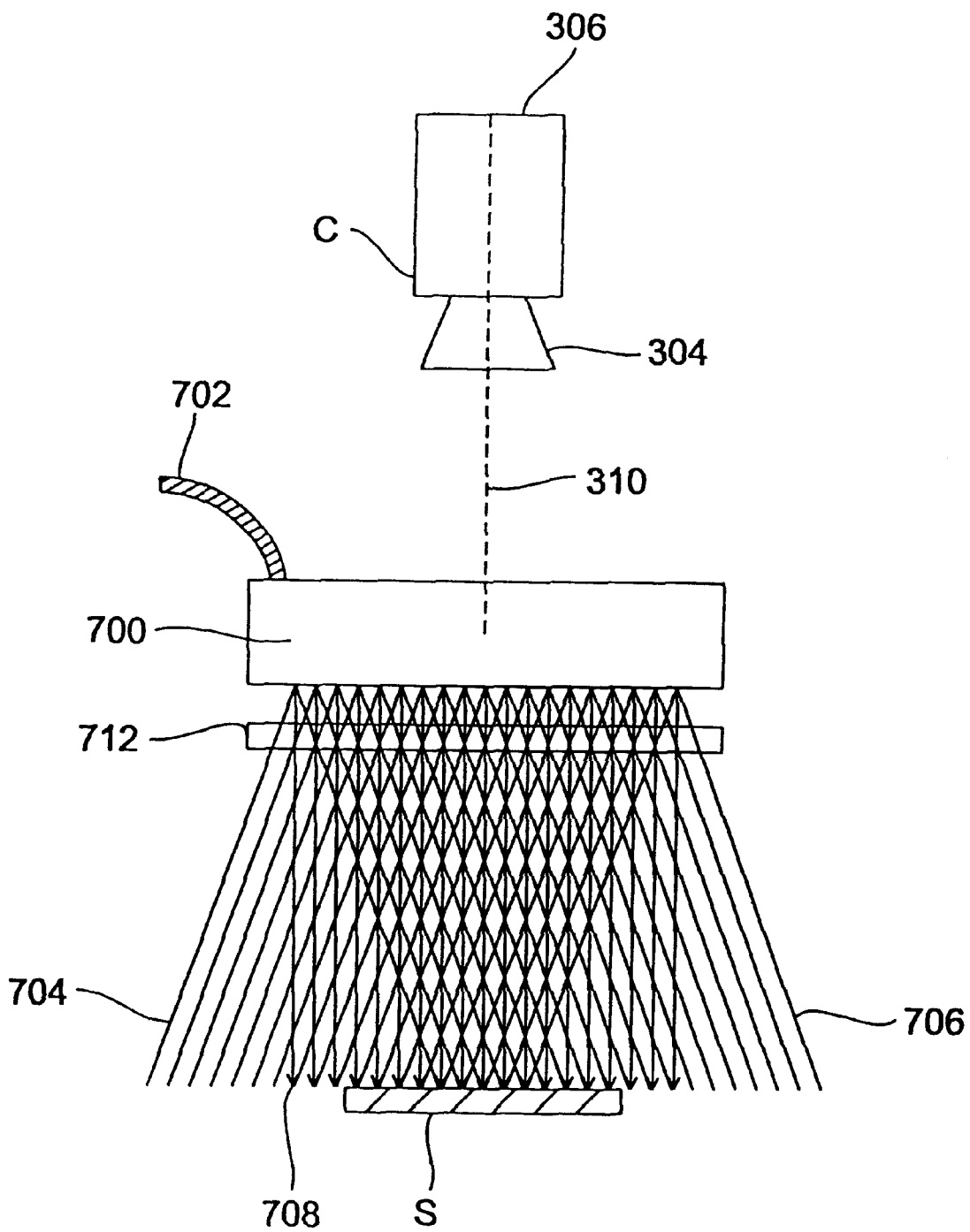

In FIG. 7 those elements which have already been described with reference to FIGS. 3 and 4 are indicated with the same reference signs and a further description is omitted. To illuminate the surface S under inspection a fibre optic 700 is used. The fibre optic is connected via a suited wave guide to a light source (not shown). The fibre optic 700 emitts light under different angles of illumination, as can be seen from FIG. 7b. A first plurality of light beams 704 and a second plurality of light beams 706 are used to achieve a dark field illumination of surface S. As becomes clear from FIG. 7b rays or beams 704 and 706, when reflected by a specular surface S having no defects are not directed towards the lens 304 of camera C. A plurality of beams 708 is directed orthogonal towards the surface S and provides the bright field illumination of surface S, since light from beam 708 is directly reflected towards the lens of camera C. In FIG. 7a the emitted light beams are shown in a side view and are indicated by reference sign 710. By means of a lens 712 or the like, the light beams are collimated.

Figure 8:
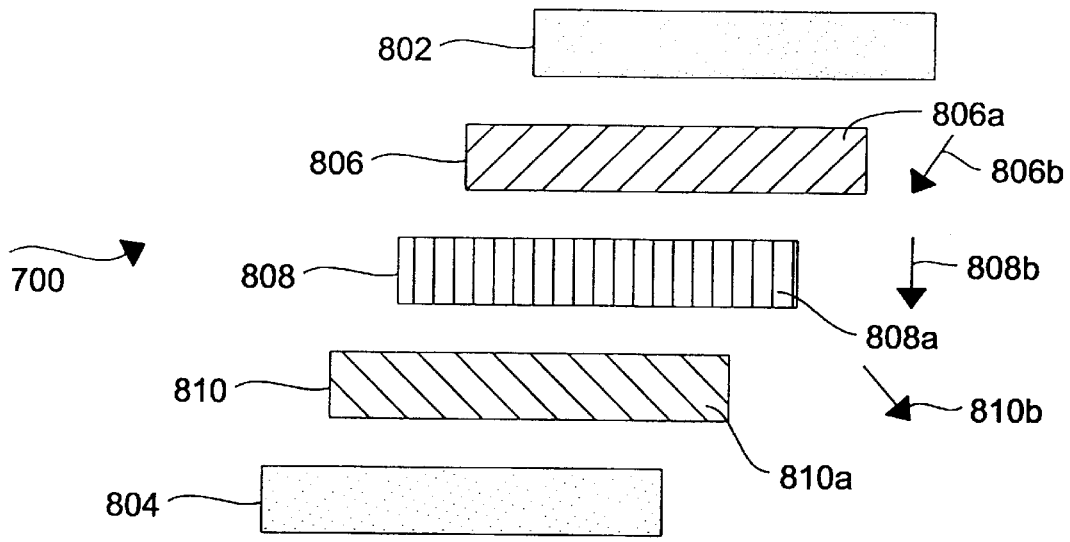
FIG. 8 shows an example of a fibre optic for illumination of the surface element under inspection.

With respect to FIG. 8 the internal structure of the fibre optic 700 is described in more detail. The fibre optic 700 comprises a first cover layer 802 and a second cover layer 804 in between which three fibre layers 806, 808 and 810 are sandwiched. Fibre layer 808 comprises, like the remaining fibre layers 806 and 810 a plurality of single fibres 808 to form a bundle of fibres which are orientated in the direction as indicated by arrow 808b. Fibre layer 806 also comprises a plurality of fibres 806a which are arranged in a tilted position when compared with the arrangement of the fibres 808a in layer 808, as it is indicated by arrow 806b. Likewise fibre layer 810 comprises a plurality of fibres 810a which are tilted with respect to the fibres 808a in layer 808, but in a different direction than the tilted fibres 806a in layer 806, as it is indicated by arrow 810*b*. In this realization the different angles of illumination are constructed inside of one single fibre illuminator. This is achieved, as shown in FIG. 8, by splitting the fibre 700 into several layers 806 to 810, wherein each of the layers 806 to 810 corresponds to one of the required channels for illumination. The different angles of illumination are achieved by tilting the fibres 806*a* and 810*a* of the respective layer 806 and 810 into the angle that corresponds to the required illumination angle, when taking Snell's law into account. It is noted that more than one layer per angle of illumination can be used. Instead of the above described embodiment using sandwiched layers of fibre optics, it is also possible to use an arrangement having one fibre layer with straight fibres for illumination under the bright field condition and to use an integrated pair of fibre layers having tilted fibres for the dark field illumination. Furthermore, three separate fibre layers for illuminating the surface under the bright field condition and under the dark field condition may be used. Besides the above described arrangement providing three different illuminations of the surface, an arrangement using e.g. two or more of the sandwiched construction of fibre layers enables an illumination of the surface in more than three directions.

It is noted that differently tilted fiber layers can be placed into separate illuminators. That is, instead of using one illuminator with three or more fiber layers, three separate illuminators with one or more fibres can be used, each with fibres tilted to proper angles. Therefore, it is possible to use three totally separate illuminators, where each has its own internal structure, i.e. its own tilting angles and as many fibre layers as needed. E.g., the first illuminator could have only straight fibres and only one layer, the second illuminator could have fibres tilted "left" 30 degrees and only one layer, and the third illuminator could have fibres tilted "right" 30 degrees and, for example, two layers. In general, the tilted fibre illuminators can produce one or more illumination directions and can consist of one or more fibre layers per illumination direction.

The arrangement shown in FIG. 8 has the following benefits:

both the camera and the illuminator can be set to an angle which is very close to the surface normal. In this case, the plane of observation and the plane of illumination almost coincide and therefore the arrangement is not sensitive to height variations and vibrations of the surface under inspection, the differently colored light components, e.g. red, green and blue, will automatically overlap and no alignment problems arise, and the structure shown in FIG. 8 is very compact and consists of only one fibre line and one cylindrical lens (see FIG. 7*a*).

In the following, the power supply for illumination by means of a fibre optic is discussed in detail. The dark field illumination used in the photometric stereo method typically requires a lot of light. The current solutions often apply high frequency or DC powered halogen lamps for the dark field illumination. These solutions are inexpensive, but the spectrum of the halogen lamps is relatively weak in the visible area, especially in the green and blue regions, and much more powerful in the near infrared and infrared portion of the spectrum.

In high speed imaging, the spectrally superior metal halide lamps are generally not used, since the normal AC powered metal halide lamps produce horizontal stripes in images, which are known as the 100 Hz modulation. This modulation is due to the fact that the metal halide lamp is practically black between the phases of the applied voltage. High frequency and DC power supplies for metal halide lamps are very expensive and typically not even available for short arc lamps with more than 100 W of power.

Figure 9:
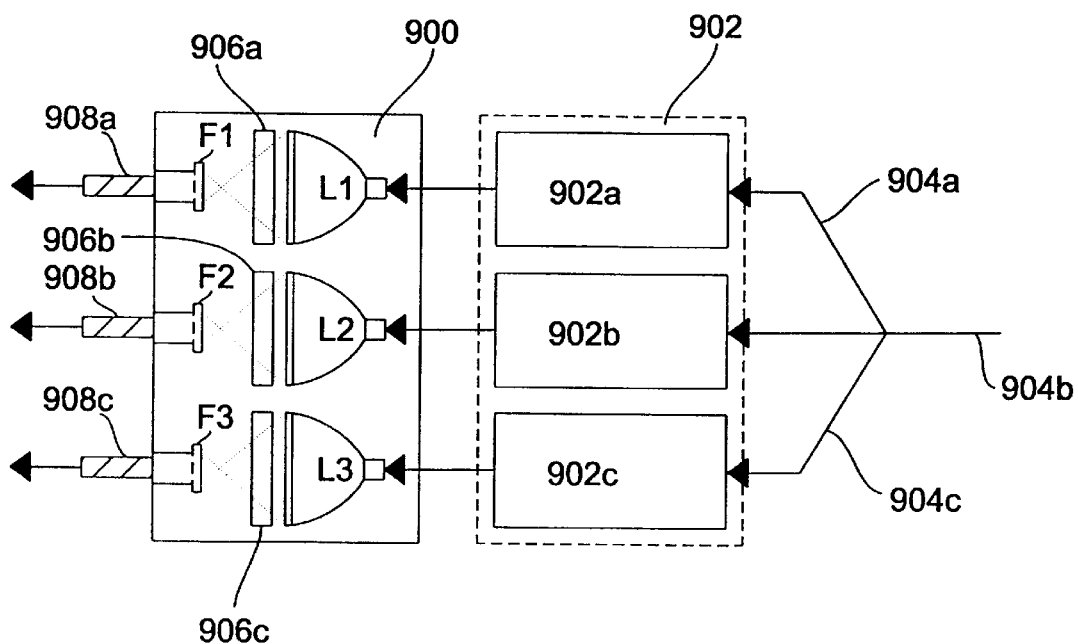
FIG. 9 shows an arrangement of a fibre optic and lamps.

With respect to FIG. 9 a new approach using metal halide lamps is described. In FIG. 9 a lamp unit 900 and a control unit 902 is shown. The lamp unit 900 includes a first, a second and a third metal halide lamp L1, L2 and L3 which are controlled by respective control elements 902*a*, 902*b* and 902*c* in the control unit 902. The control elements 902*a* through 902*c* receive via lines 904*a*, 904*b* and 904*c* a power. The power applied to the respective control elements 902*a* to 902*c* are different in phase. Each lamp L1, L2 and L3 is provided with either ellipsoid reflectors or focusing lenses to focus the light emitted from the lamps L1, L2 and L3 to associated filter elements F1, F2 and F3 to provide a lamp unit output on fibre bundles 908*a*, 908*b* and 908*c* of different color. Optional IR-filters 906*a*, 906*b* and 906*c* can be used to block the IR-component of light to protect the fibre bundles from extra heat.

The control unit 902 controls the metal halide lamps L1 through L3 by a three phase AC power applied via lines 904*a*, 904*b* and 904*c*. The lamps are connected to a fibre line having the fibre bundles 908*a*, 908*b* and 908*c*, wherein the fibre line has a randomized fibre construction. The lamps are connected to the fibre line in groups of three lamps so that each of these lamps is running at a 120° phase shift compared to the others. If the fibres are properly randomized in the fibre line, the resulting illumination output is not zero at any time, and this results in a reduced amount of ripples in the image. The remaining ripples can be easily removed from the image by well known means of analog or digital signal processing. The arrangement shown in FIG. 9 has the benefit that efficient metal halide lamps can be used without limiting and expensive accessoires.

Figure 10:
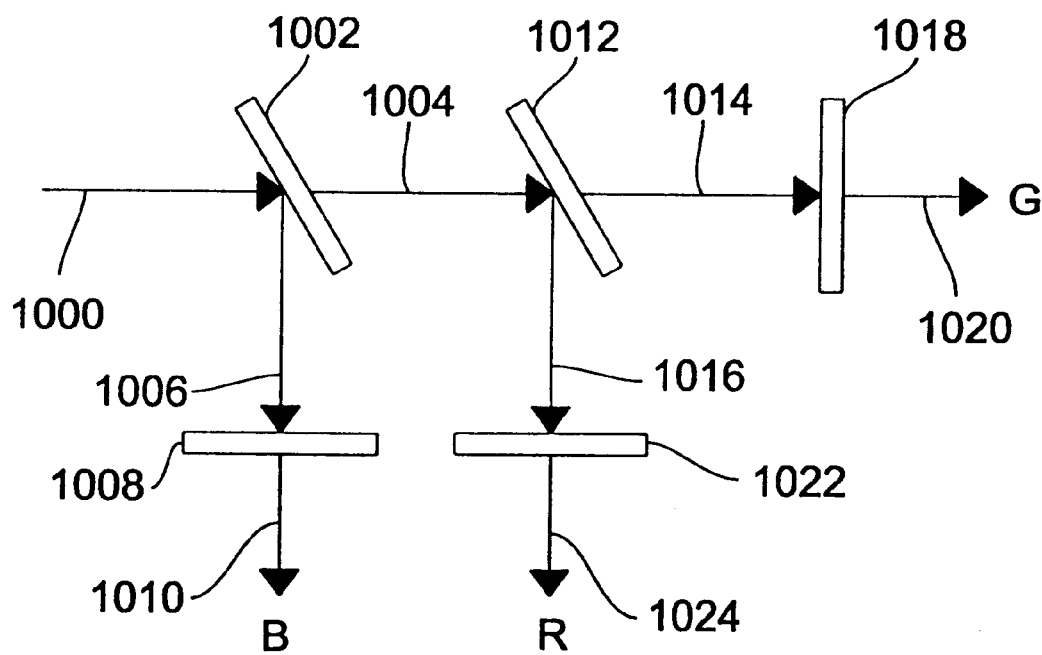
FIG. 10 shows an arrangement for deriving the beams of light of different color from a single light source.

In the construction shown in FIG. 9, the differently colored light components are produced by the color filters F1, F2 and F3 and separate lamps L1, L2 and L3 are used for each color. However, such an arrangement wastes a lot of illumination power since only a narrow range of the spectrum is bandpassed through the filter and fed to the fibre line. Instead of the arrangement shown in the lamp unit 900, a preferred choice is to use an arrangement as it will be described with reference to FIG. 10. Further to the above described metal halide lamps any AC-driven lamps can be used. With respect to FIG. 10 an arrangement is shown, which uses only one lamp to produce the three colors. A beam of light 1000 from a lamp (not shown) is directed onto a blue-reflective filter 1002 which transmit only light of red and green color as indicated by arrow 1004 and reflects light of blue color as indicated by arrow 1006. The blue light is then again filtered by means of a blue filter 1008 and at a first output 1010 the blue light is output. The red and green light beam is directed to a red-reflective filter 1012 which transmits green light as indicated by arrow 1014 and reflects red light as indicated by arrow 1016. The transmitted green light is passed through a green filter 1018 and at a second output 1020 a beam of green light is output. The red light reflected by filter 1012 is directed to a red filter 1022 and at a third output 1024 a beam of red light is output. As can be seen from FIG. 10 all color components are produced from one single lamp and in this case, the amount of lamps can, in principle, reduced by a factor of three. If appropriate dichroidic filters are used, the additional color filters 1008, 1018 and 1022 are not needed.

Figure 11:
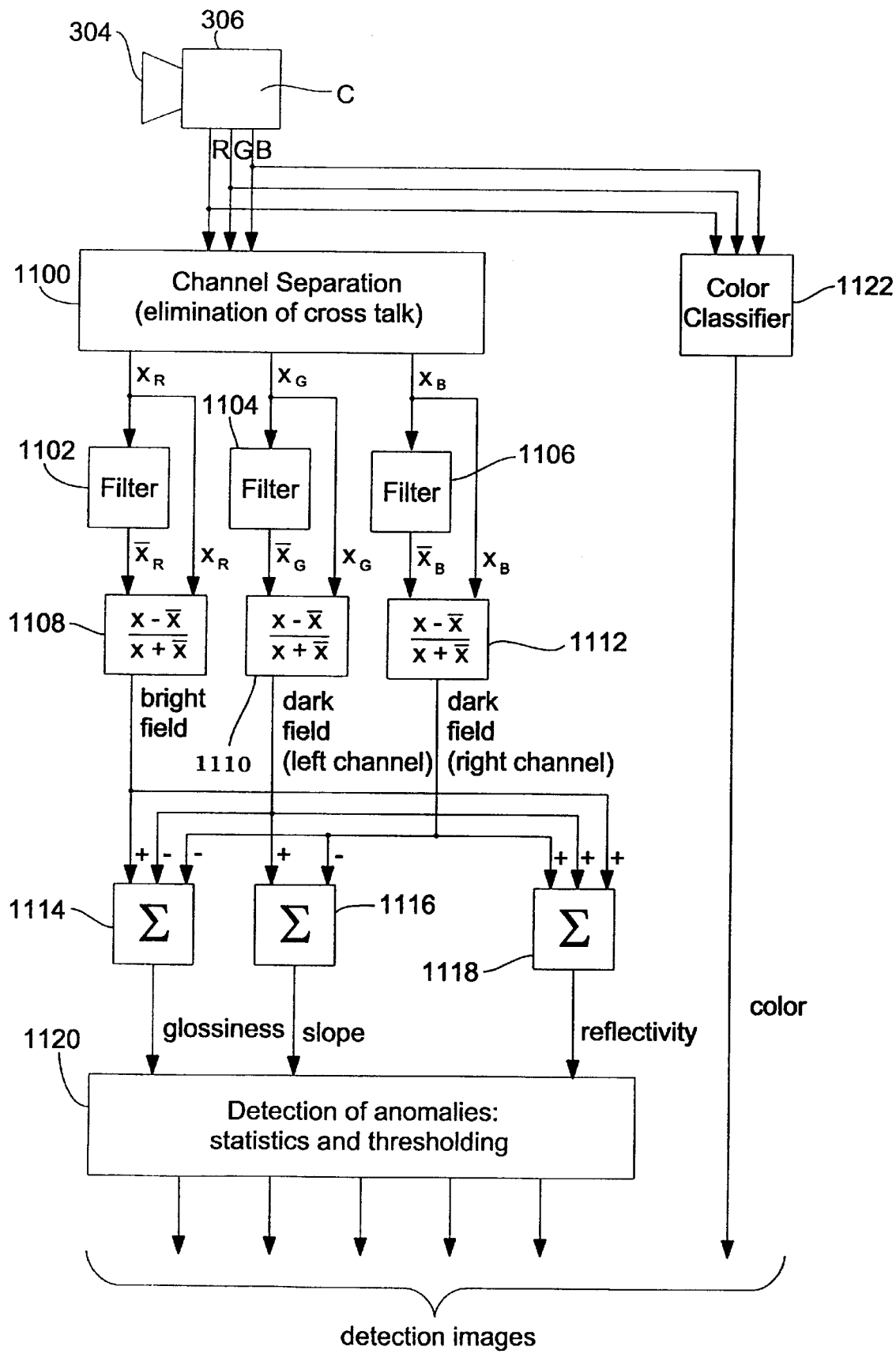
FIG. 11 illustrates the signal processing chain for detection of anomalies based on the obtained signal.

With respect to FIG. 11 the estimation of physical properties of a surface element under inspection according to the present invention is now described.

FIG. 11 shows a block diagram of the first three steps S100, S102, and S104 as described with reference to FIG. 1. The signals acquired by means of the camera C are in the described embodiment signals representing a red image (R), a green image (G) and a blue image (B). The three images are input into block 1100 in which a channel separation is carried out. For the description of FIG. 11 it ist assumed that the bright field illumination of the surface results in the red image, and that the dark field illumination results in a green image for the left channel (light source L2 in FIG. 3) and in a blue image for the right channel (light source L3 in FIG. 3). Block 1100 outputs three separated signals representative of the influence of the three channels of illumination. The signals $X_R$, $X_G$ and $X_B$ are input into respective filters 1102, 1104 and 1106, as well as into respective blocks 1108, 1110, 1112 for expressing deviations in the signals not as differences from the average but as contrast. The calculations carried out in block 1108, 1110 and 1112 are made on the basis of the signals received from block 1100 and on the signals received from the respective filters 1102, 1104 and 1106 which output an average signal value of the signal output from block 1100. Block 1108 outputs a signal representative of the bright field, block 1110 outputs a signal representative of the left channel dark field and block 1112 outputs a signal representative of the right channel dark field. These signals are input into blocks 1114, 1116 and 1118. Block 1114 substracts from the bright field the dark field for the left channel and for the right channel and outputs a signal representing the glossiness of the inspected surface element. Block 1118 forms a difference between the left channel dark field and the right channel dark field and outputs a signal representing the slope in the surface under inspection. Block 1118 sums the bright field and the two dark fields and outputs a signal representative of the reflectivity of the surface under inspection. The signals indicative of the glossiness, slope and reflectivity are input into block 1120 which detects anomalies on the basis of specific statistics and by thresholding the received signals. Block 1120 outputs further signals for the further processing described with reference to FIG. 1, namely the feature extraction, the classification and decision. The signals R, G and B from the camera C are also input into a color classifier 1122 which outputs a signal indicating miscolored regions of the surface which is also used for the further processing of the detection images output by block 1120.

As becomes clear from the above description of FIG. 11, the first aim is to estimate the physical properties of the surface element under inspection from the video signal (R, G, B) of the camera C.

In general, the spectral distribution of the three channels R, G, B of the color line scan camera C will show some overlap and/or the spectral distribution of the light sources will not meet exactly the color channels of the camera C. As a result, there will be some crosstalk between the three channels of illumination which can be eliminated by measuring the crosstalk for a non-defective surface and substracting for each channel R, G, B the respective fractions of crosstalk from the other two channels, which is carried out in block 1100.

In most of the applications, it is not necessary to measure absolute values of figures for the reflectivity or the slope of the surface element under inspection. Instead, local deviations from the average appearance of the surface have to be detected. This is achieved by the stage of adaptive filters 1102, 1104 and 1106 following the channel separation 1100. Dependent of the needs of the application, the filters may e.g. be low pass filters or moving average filters. By calculating in blocks 1108, 1110 and 1112 $(x-x)/(x+x)$ for each channel, the deviations are not expressed as differences from the average but as contrast. The advantage is that the results are not effected by the absolute level of illumination or the sensitivity of the camera C. Furthermore, the three channels are scaled in the same way, regardless of e.g. the changing balance of the three channels of illumination, which is essential for the following processing step.

The result of the above described stage of signal processing are scaled images representing the deviations from the average appearance for the three channels, namely the bright field, the left dark field and the right dark field. From these images the reflectivity, glossiness and slope of the surface element under inspection is estimated by blocks 1114, 1116 and 1118 as follows:

The reflectivity is the sum of all three channels, namely the total reflected light energy, the glossiness is the bright field minus the sum of the dark field, which yields a high glossiness for a slim distribution of reflected light, and a low glossiness for a broad distribution of light (see FIG. 2), and the slope is determined by forming the difference between the left dark field and the right dark field, i.e. by checking the balance of the dark fields or the symmetry of the reemitted light distribution.

In conjunction with the output image of the color classifier, these three images carry the information on the physical properties of the surface in an explicit expression with the same spatial resolution as the original image.

FIG. 12 shows an example of the generation of an image representing the slope in a surface. With respect to FIG. 12 a left dark field image and a right dark field image are shown as well as the resulting image showing slopes and other 3D-defects on the surface.

Figure 12A:
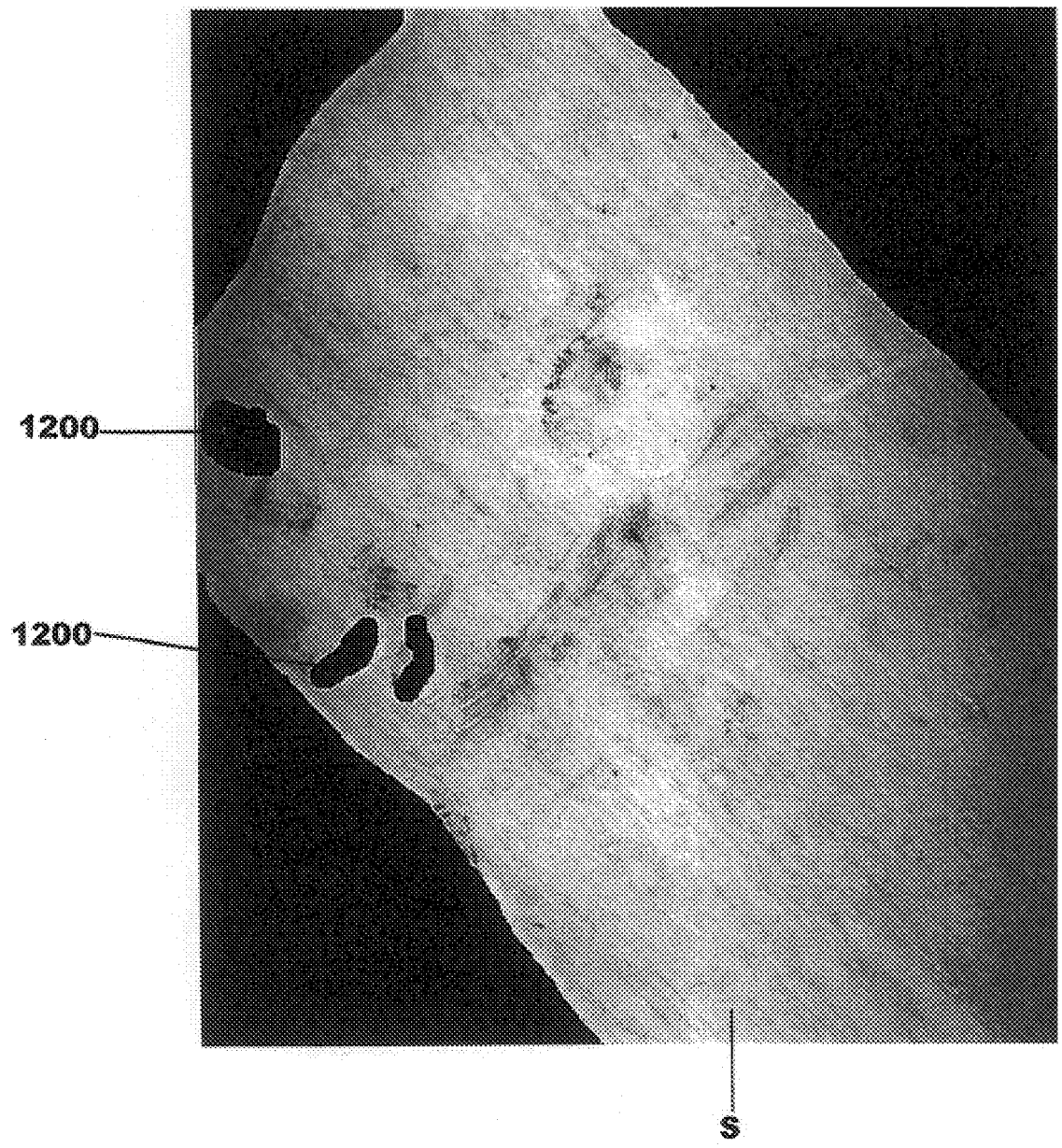
FIG. 12a shows a photographic representation obtained from the first dark field channel.
Figure 12B:
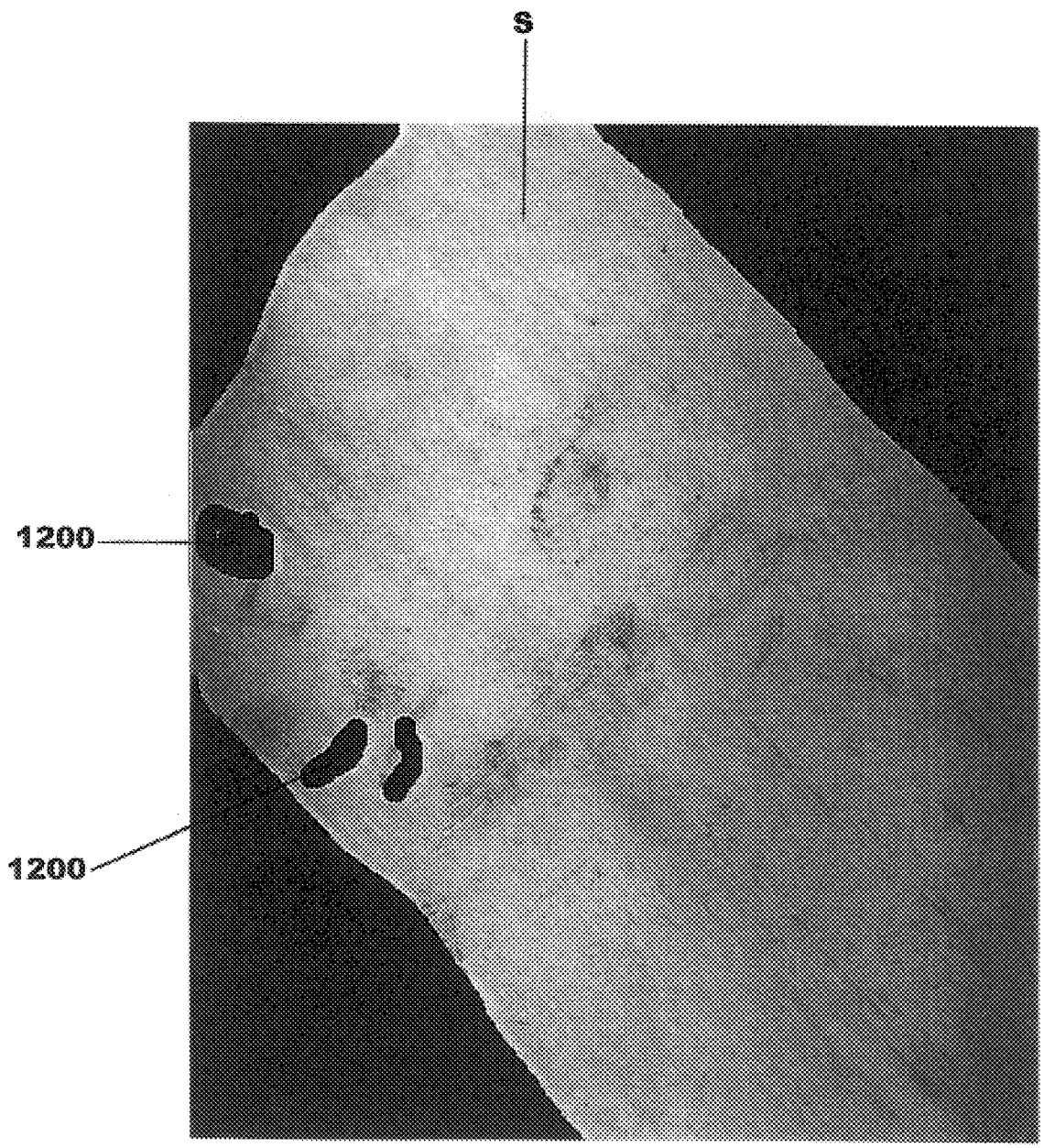
FIG. 12b shows a photographic representation obtained from the second dark field channel.
Figure 12C:
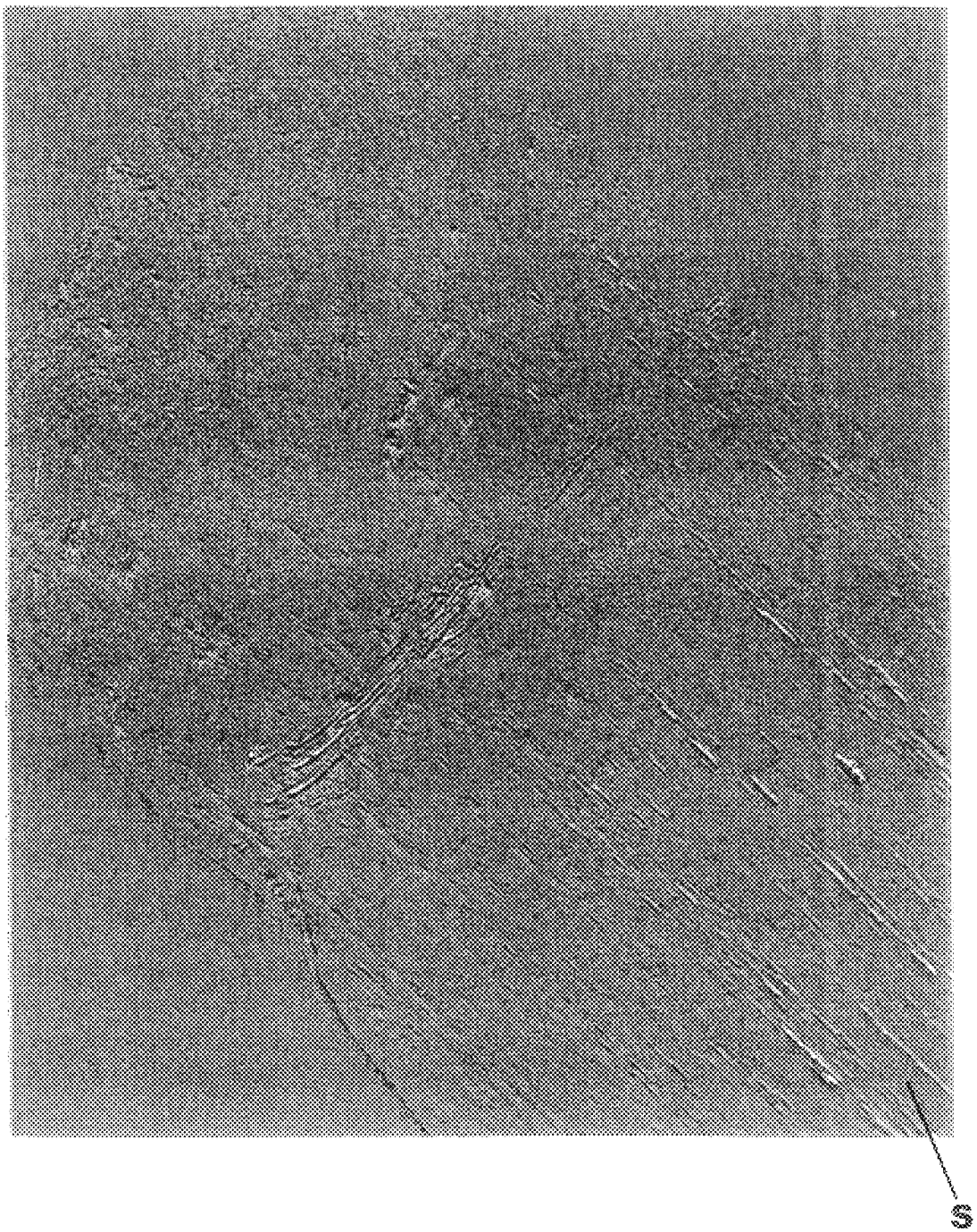
FIG. 12c shows a photographic representation showing 3D-defects in the surface obtained from the images shown in FIG. 12a and FIG. 12b by applying the steps described in FIG. 11.

FIG. 12a shows the image of the left dark field. As can be seen a surface S has some spots 1200 thereon, which are e.g. oil spots. FIG. 12b shows the image of the right dark field which is substantially identical. FIG. 12c illustrates the resulting image after the method described with reference to FIG. 11 has been applied. What can be seen in FIG. 12c is the surface S without the oil spots which are suppressed, and that the 3D-structure of the surface is shown in detail. The image shown in FIG. 12c is the output of block 1116 and called a relief image.

Anomalies in the inspected surface, defect candidates, can be detected by simply thresholding the images representing reflectivity, glossiness, slope or color (see block 1120 in FIG. 11). For some classes of defects this will not be the appropriate method for defect detection, e.g. for waves, shallow sloping regions on the surface, or for estimation of surface roughness. For such types of defects it is advantageous to apply statistical measurements, which are tailored to the characteristic features of the considered classes of defects. E.g. the mean value of the slope image formed by block 1116 is calculated within a moving window for detection of shallow sloping regions, or the standard deviation of the slope image formed by block 1116 within a moving window is calculated for estimation of the surface roughness. The size of the moving window is adapted to the size of the considered class of defects. For each pixel, the results of the statistical measurements are compared with a threshold.

The result of this stage of signal processing are detection images which carry condensed information on local or regional anomalies of the inspected surface, related to the physical properties reflectivity, glossiness, slope and color. It is the advantage of the present invention that this information can be extracted with high reliability, high speed and high spatial resolution.

In the following, the application of the inventive method and the inventive apparatus to a steel production will be described.

Automatic visual inspection is used in steel and other metal (aluminium, copper) rolling mills to replace and aid visual inspections made by operators. The typical characteristics of rolled, flat strip have large variations:

width . . . 100 mm–2500 mm,
thickness . . . 0.1 mm–25 mm, and
process line speed . . . 5 m/min–1500 m/min.

The strips need to be inspected in several process stages during the manufacturing to prevent the production of scrap:
hot rolling (T: 500° C.–1000° C.),
pickling and annealing processes (T<100° C.),
cold rolling (T<50° C.),
coating (galvanizing, tin plating, painting, T<100° C.),
cutting and splitting, and
final inspections before the delivery to customers, often special inspection lines are used.

There are a large number of various visual surface defects being critical for the quality of the strip:
metallurgical defects caused by impurities and weaknesses in the internal structure of the metal that have become visible during the rolling processes (eg. slivers, scales slags and through holes)
defects caused by the rolling processes like repeating roll marks, dents, scratches and uneven coating, and
defects caused by the mechanical handling.

The defect lengths and widths can vary from 0.1 mm up to several meters. Many defects are elongated in the rolling direction so typically the defect length is bigger than its width. Often the critical defects are not flat but have three dimensional shapes due to broken surface or local dents. The defect depths vary from tens of microns to through holes.

The visual appearance of a defectless metal strip is seldom homogeneous. There are typically dirt stripes, oil spots, uneven reflectance and texture on the surface that can be easily confused with the real defects. Often the human inspectors have to stop the strip and touch the surface by hand to find out if the defect has critical 3D-characteristics. At higher line speeds human visual inspections are very unreliable and no 100% inspection can be guaranteed.

There are continuously increasing trends to improve the quality of the metal strips driven by demanding customers like automotive industries using thinner strips and targeting to high quality.

It has proved very difficult to apply automatic optical inspection in metal strip manufacturing. There are several systems in the market using either laser scanning or CCD line scan cameras but no real breakthrough has been reached. Often the systems have several cameras (or detectors) to view the surface from different directions but their capabilities to analyze the 3D shapes of the defects are very limited. Basically the systems based on the current 2D-technology are capable to detect the defects but they are not good enough to discriminate between real defects and non-important "pseudodefects". The complicated image processing and pattern recognition methods are used in defect analysis and classification to compensate the weaknesses in the basic measurement. Every defect type needs its own parameters and laborous and time consuming "teaching" periods are needed to train the automatic inspection system. Even in the best cases it takes a long time and needs great efforts to reach satisfactory results. As a consequence, most of the metal rolling mills have no resources to apply the current surface inspection technology.

The present invention improves decisively the quality of the measurement signal producing a much more viable basis to automatically identify the critical defects. The possibility to directly measure the 3D-characteristics of defects will shorten drastically the start-up periods of the systems being the major hindrance of the current technology. Also the detection performance of small defects is improved due to better measurements.

In the above described preferred embodiments the surface was illuminated by light of different colors. The present invention is however not limited to these characteristics of the used light beams. Instead of light of different color, light having a different polarization can be used.

The above described preferred embodiments of the present invention use only one color line scan camera and multiple channels of illumination, and the signal acquisition and processing is based on the idea of photometric stereo.

In a further embodiment (not shown) it is possible to use instead of the arrangement shown in FIGS. 3 and 4 an arrangement which uses one illumination source and a plurality of sensor devices, like cameras each outputting one signal. In this case, the first illumination/observation channel is formed by a first light sensitive sensor device and a light source, wherein the first light sensitive sensor device receives light of a first characteristic reemitted from the surface element, wherein the first light source illuminates the surface element. The second illumination/observation channel is formed by a second light sensitive sensor device and the light source, wherein the second light sensitive sensor device receives light of a second characteristic reemitted from the surface element. The third illumination/observation channel is in this embodiment formed by a third light sensitive sensor device and the light source, wherein the third light sensor device receives light of a third characteristic reemitted from the surface element. With other words, this embodiment uses only one light source and three light sensitive sensor devices receiving reemitted light of different characteristics from the surface. The first, second and third light sensitive sensor devices are spatially separated from each other.

What is claimed is:

1. Method for automatic inspection of moving surfaces using at least three different illumination/observation channels, said method comprising the steps of:
   a) illuminating said surface to be inspected under a bright field condition by a first beam of light from a first light source, and receiving light of the first beam of light reemitted from said surface by a light sensitive sensor device to obtain a first signal;
   b) illuminating said surface under a dark field condition by a second beam of light and by a third beam of light from a second and a third light source, respectively, said first, second and third beams of light having different characteristics, and receiving light of the second beam of light and light of the third beam of light, respectively, reemitted from said surface by said light sensitive sensor device to obtain a second signal and a third signal; and
   c) deriving from said first, second and third signals a physical property of said surface.

2. Method according to claim 1, wherein said first, second and third beam of light have different spectral characteristics.

3. Method according to claim 1, wherein said illumination of said surface by said second and third beam of light is symmetrical with respect to the first beam of light illuminating said surface, with respect to the normal of the surface, or with respect to the direction of observation.

4. Method according to claim 1, wherein said physical property of said surface derived from said first, second and third signals includes reflectivity, glossiness and slope of said surface.

5. Method according to claim 4, wherein information on said reflectivity of said surface is derived from the sum of the first, second and third signal;

information on said glossiness of said surface is derived from the first signal minus the sum of the second and third signals; and information on said slope of said surface is derived from the difference of the second and the third signals.

6. Method according to claim 5, comprising the following steps prior to deriving information on the reflectivity, glossiness and slope of said surface:

filtering the first, second and third signal; and calculating normalized differences for each signal to scale the signals in the same way.

7. Method according to claim 1, comprising the step of detecting anomalies of the surface on the derived physical property.

8. Method according to claim 7, wherein said step of detecting comprises the following steps:

calculating statistical features from the derived physical property; and comparing the derived physical property with a threshold.

9. Method for automatic inspection of moving surfaces using at least three different illumination/observation channels, said method comprising the steps of:

a) illuminating said surface by a beam of light from a light source;

b) receiving light of a first characteristic reemitted from said surface under a bright field condition by a first light sensitive sensor device to obtain a first signal;

c) receiving light of a second and a third characteristic, respectively, reemitted from said surface under a dark field condition by a second and a third light sensitive sensor device to obtain a second signal and a third signal, said first, second and third light sensitive sensor devices being spatially separated from each other; and d) deriving from said first, second and third signals a physical property of said surface.

10. Apparatus for automatic inspection of moving surfaces, comprising a first light source illuminating said surface with light of a first spectral characteristic under a bright field condition;

a light sensitive sensor device receiving reemitted light of the first spectral characteristic to obtain a first signal;

a second light source illuminating said surface with light of a second spectral characteristic under a dark field condition, said second spectral characteristic being different from said first spectral characteristic, said light sensitive sensor device receiving reemitted light of the second spectral characteristic to obtain a second signal;

a third light source illuminating said surface with light of a third spectral characteristic under a dark field condition, said third spectral characteristic being different from said first and second spectral characteristics, said light sensitive sensor device receiving reemitted light of the third spectral characteristic to obtain a third signal; and means for deriving a physical property of said surface from said first, second, and third signals.

11. Apparatus according to claim 10, wherein said second and third light source are arranged symmetrically with respect to a light beam of said first light source, with respect to the normal of the surface, or with respect to the direction of observation.

12. Apparatus according to claim 10, wherein said physical property of said surface includes reflectivity, glossiness and slope of said surface.

13. Apparatus according to claim 12, wherein said means for deriving a physical property comprises:

means for summing the first, second and third signal to provide a signal representing the reflectivity of said surface;

means for forming a difference between the first signal and the sum of the second and third signal to provide a signal representing the glossiness of said surface; and means for forming a difference between the second and third signal to provide a signal representing the slope of said surface.

14. Apparatus according to claim 10, wherein said means for deriving a physical property comprises means for detecting anomalies of said surface based on the derived physical property.

15. Apparatus according to claim 10, wherein said first, second and third light sources are formed by one or a plurality of fibre optic means, each fibre optic means having at least one fibre layer, the fibre optic means and the fibre layers thereof being arranged such that light of said first, second and third light sources illuminates said surface under predetermined illumination angles.

16. Apparatus according to claim 10, wherein said first, second and third light sources are formed by fibre optic means, said fibre optic means comprising at least three layers, a first layer providing light of the first spectral characteristic, a second layer providing light of the second spectral characteristic and a third layer providing light of the third spectral characteristic, wherein said first and third layer are tilted with respect to the second layer such that light of the first and third spectral characteristic illuminates said surface under predetermined illumination angles.

17. Apparatus according to claim 10, wherein said first, second and third light sources are formed by a first and a second fibre optic means, said first fibre optic means comprising at least one layer providing light of the first spectral characteristic, said second fibre optic means comprising at least two layers providing light of the second spectral characteristic and the third spectral characteristic, wherein said fibre layers of the second fibre optic means providing the light of the second and third characteristic are tilted with respect to the layer of the first fibre optic means such that light of the second and third spectral characteristic illuminates said surface under predetermined illumination angles.

18. Apparatus according to claim 10, wherein said first, second and third light sources comprise AC-driven lamps connected to randomized fibre line in groups of three lamps, wherein each lamp is controlled to be operated at a 120° phase shift with respect to the remaining two lamps.

19. Apparatus according to claim 18, wherein said AC-driven lamps are metal halide lamps.

20. Apparatus according to any of claims 10, wherein said first, second and third light sources are formed by a lamp, said lamp comprising a beam splitter means to obtain at least three different light beams having different spectral characteristics.

21. Apparatus according to claim 20, wherein said beam splitter means comprises dichroitic mirrors and filters for the different spectral characteristics.

22. Apparatus for automatic inspection of moving surfaces, comprising a light source for illuminating said surface;

a first light sensitive sensor device receiving light of a first spectral characteristic reemitted from said surface under a bright field condition to obtain a first signal;

a second light sensitive sensor device receiving light of a second spectral characteristic reemitted from said surface under a dark field condition to obtain a second signal, said second spectral characteristic being different from said first spectral characteristic;

a third light sensitive sensor device receiving light of a third spectral characteristic reemitted from said surface under a dark field condition to obtain a third signal, said third spectral characteristic being different from said first and second spectral characteristic, said first, second and third light sensitive sensor devices being spatially separated from each other; and means for deriving a physical property of said surface from said first, second, and third signals.

* * * * *